United States Patent
Yun

(10) Patent No.: US 10,800,831 B2
(45) Date of Patent: Oct. 13, 2020

(54) SYSTEMS AND METHODS FOR OBTAINING INFORMATION ASSOCIATED WITH AN ANATOMICAL SAMPLE USING OPTICAL MICROSCOPY

(71) Applicant: The General Hospital Corporation, Boston, MA (US)

(72) Inventor: Seok-Hyun Yun, Cambridge, MA (US)

(73) Assignee: The General Hospital Corporation, Boston, MA (US)

( * ) Notice: Subject to any disclaimer, the term of this patent is extended or adjusted under 35 U.S.C. 154(b) by 645 days.

(21) Appl. No.: 15/599,662

(22) Filed: May 19, 2017

(65) Prior Publication Data

US 2017/0254749 A1    Sep. 7, 2017

Related U.S. Application Data

(63) Continuation-in-part of application No. PCT/US2015/061593, filed on Nov. 19, 2015, and a
(Continued)

(51) Int. Cl.
*A61B 5/00* (2006.01)
*C07K 14/705* (2006.01)
(Continued)

(52) U.S. Cl.
CPC ........ *C07K 14/70503* (2013.01); *A61B 3/102* (2013.01); *A61B 3/117* (2013.01); *A61B 5/0059* (2013.01); *A61B 5/0066* (2013.01); *A61B 5/0073* (2013.01); *A61B 5/0084* (2013.01); *A61B 5/0095* (2013.01); *A61B 5/412* (2013.01); *A61B 5/413* (2013.01); *G01B 9/02091* (2013.01); *G01J 3/4412* (2013.01); *G01N 21/1717* (2013.01); *G01N 21/4795* (2013.01);
(Continued)

(58) Field of Classification Search
CPC ................................ A61B 3/102; A61B 3/117
See application file for complete search history.

(56) References Cited

U.S. PATENT DOCUMENTS

3,813,613 A    5/1974   Danielmeyer et al.
4,483,005 A    11/1984  Smart
(Continued)

FOREIGN PATENT DOCUMENTS

| JP | 2003102672 A | 4/2003 |
| JP | 2003535659 A | 12/2003 |
| WO | 2005047813 A1 | 5/2005 |

OTHER PUBLICATIONS

International Search Report and Written Opinion issued in correcponding International Application No. PCT/US2015/061593 dated Feb. 3, 2016, 12 pages.
(Continued)

*Primary Examiner* — Joseph M Santos Rodriguez
(74) *Attorney, Agent, or Firm* — Quarles & Brady LLP

(57) ABSTRACT

This disclosure provides systems and methods for mapping and/or measuring a mechanical property of a medium. The mechanical property can be measured by Brillouin spectroscopy. The systems and methods can include a three-dimensional imaging modality that is co-registered with a Brillouin probe beam of a Brillouin spectrometer. The three-dimensional imaging modality can be optical coherence tomography or Scheimpflug camera imaging.

24 Claims, 18 Drawing Sheets

Related U.S. Application Data continuation-in-part of application No. 11/672,571, filed on Feb. 8, 2007, now Pat. No. 9,777,053.

(60) Provisional application No. 62/081,963, filed on Nov. 19, 2014, provisional application No. 60/771,916, filed on Feb. 8, 2006.

(51) Int. Cl.
| | |
|---|---|
| *G01J 3/44* | (2006.01) |
| *G01N 21/17* | (2006.01) |
| *G01N 21/63* | (2006.01) |
| *G01N 21/47* | (2006.01) |
| *A61B 3/10* | (2006.01) |
| *A61B 3/117* | (2006.01) |
| *G01B 9/02* | (2006.01) |
| *G02B 21/00* | (2006.01) |

(52) U.S. Cl.
CPC .......... *G01N 21/636* (2013.01); *A61B 5/0075* (2013.01); *A61B 5/0086* (2013.01); *A61B 5/0097* (2013.01); *A61B 5/4088* (2013.01); *C07K 2319/30* (2013.01); *C07K 2319/32* (2013.01); *C07K 2319/70* (2013.01); *G01N 2021/1725* (2013.01); *G01N 2021/638* (2013.01); *G01N 2201/06* (2013.01); *G01N 2201/0612* (2013.01); *G01N 2800/042* (2013.01); *G01N 2800/387* (2013.01); *G01N 2800/7023* (2013.01); *G01N 2800/7028* (2013.01); *G02B 21/0052* (2013.01)

(56) References Cited

U.S. PATENT DOCUMENTS

| | | |
|---|---|---|
| 5,912,179 A | 6/1999 | Alvarez et al. |
| 6,002,480 A | 12/1999 | Izatt et al. |
| 6,134,003 A | 10/2000 | Tearney et al. |
| 7,355,716 B2 | 4/2008 | de Boer et al. |
| 7,382,949 B2 | 6/2008 | Bouma et al. |
| 7,480,058 B2 | 1/2009 | Zhao et al. |
| 7,777,891 B2 | 8/2010 | Hasegawa |
| 8,422,023 B2 | 4/2013 | Podoleanu |
| 2009/0054763 A1 | 2/2009 | Wang et al. |
| 2014/0078512 A1 | 3/2014 | Kang et al. |

OTHER PUBLICATIONS

Randall et al. "Brillouin scattering in systems of biological significance" Philosophical Transactions of The Royal Society London, vol. 293, 1979, pp. 341-348, XP009086852.

Takagi et al. "Application of a microscope to Brillouin scattering spectroscopy" Review of Scientific Instruments, AIP, Melville, NY, US. vol. 63, No. 12, Dec. 1, 1992, pp. 5552-5555, XP000330413, ISSN: 0034-6748.

J.M. Vaughan et al. "Brillouin scattering, density and elastic properties of the lens and cornea of the eye," Nature, vol. 284, Apr. 3, 1980, pp. 489-491.

SYSTEMS AND METHODS FOR OBTAINING INFORMATION ASSOCIATED WITH AN ANATOMICAL SAMPLE USING OPTICAL MICROSCOPY

CROSS-REFERENCE TO RELATED APPLICATIONS

This application is based on and claims priority to International Application No. PCT/US2015/061593 filed Nov. 19, 2015, which is based on and claims priority to U.S. Provisional Application Ser. No. 62/081,963, filed Nov. 19, 2014. This application is also a continuation-in-part of U.S. patent application Ser. No. 11/672,571 filed Feb. 8, 2007, which is based on and claims priority to U.S. Provisional Application Ser. No. 60/771,916, filed Feb. 8, 2006.

STATEMENT REGARDING FEDERALLY SPONSORED RESEARCH

N/A

BACKGROUND OF THE INVENTION

The present disclosure generally relates to improvements to the accuracy and precision of Brillouin microscopy techniques. Specifically, the present disclosure relates to systems and methods that improve the accuracy and precision of Brillouin microscopy by co-registering a 3-dimensional imaging modality, and using the imaging information to more accurately determine the location of the focus of the Brillouin probe beam, thereby improving the Brillouin maps that are generated by the Brillouin microscopy.

Existing Brillouin microscopy systems can include a video camera and a side-illuminating light emitting diode (LED) to determine the x, y coordinate of the Brillouin laser beam with an accuracy of 200 µm. The axial location of the beam or the distance of the corneal surface from an objective lens (for example, a Mitytoyo 5× infinity-corrected long working distance objective lens) is determined by the size of the specular reflected LED beam. When the size of this reflected beam is minimized, the operator knows that the focus is located at the corneal surface. The x, y, z control is executed in existing systems by an operator moving the scanning head of the Brillouin scanner. This manual alignment method can be slow and/or inaccurate. Often the operator has to take a large number of axial scans at arbitrary locations, and often the axial scan starts from a distance from the corneal surface, thereby causing longer scan times than necessary. Furthermore, patient movement during axial scans (which can take 1-20 s with 0.1-0.4 s per pixel) can cause errors and cannot be corrected because the z-coordinate during the scan is unknown.

There exists a clear need for improvements that allow the z-coordinate to be accurately measured and utilized in Brillouin microscopy measurements.

SUMMARY OF THE INVENTION

The present invention overcomes drawbacks of previous technologies by providing systems and methods for obtaining information associated with an anatomical sample using optical microscopy.

In one aspect, the present disclosure provides a method of mapping a mechanical property of a medium. The method can include one or more of the following steps: a) scanning a focal point of a multiplexed optical beam along an axial direction through the medium, the multiplexed optical beam comprising a Brillouin probe beam and an imaging sample beam; b) receiving a Brillouin signal generated by the Brillouin probe beam and an imaging signal generated by the imaging sample beam; c) determining, using a processor and the Brillouin signal, the mechanical property of the medium for at least one point along the axial direction; and d) determining, using the processor and the imaging signal, a depth of the at least one point along the axial direction. The imaging sample beam can be an optical coherence tomography (OCT) sample beam or a Scheimpflug sample beam. The imaging signal can be an OCT signal or a Scheimpflug signal.

In another aspect, the present disclosure provide a method of measuring a mechanical property of a medium. The method can include one or more of the following steps: a) focusing a Brillouin probe beam of a Brillouin spectrometer to a focus at a depth or a plurality of different depths in the medium; b) acquiring real-time information on the depth or the plurality of different depths using a three-dimensional imaging system; c) receiving a Brillouin signal generated by the Brillouin probe beam; and d) determining, using a processor and the Brillouin signal, the mechanical property of the medium at the depth or the plurality of different depths. The three-dimensional imaging system can be an OCT system or a Scheimpflug system.

In yet another aspects, the present disclosure provides an optical system. The optical system can include a Brillouin microscope having a Brillouin probe beam and a three-dimensional imaging system having an imaging sample beam, wherein the Brillouin probe beam and the imaging sample beam are a multiplex and/or co-registered beam. The three-dimensional imaging system can be an OCT system or a Scheimpflug system. The imaging sample beam can be an OCT sample beam or a Scheimpflug sample beam.

The foregoing and other advantages of the disclosure will appear from the following description. In the description, reference is made to the accompanying drawings which form a part hereof, and in which there is shown by way of illustration a preferred embodiment of the disclosure. Such embodiment does not necessarily represent the full scope of the disclosure, however, and reference is made therefore to the claims and herein for interpreting the scope of the disclosure.

BRIEF DESCRIPTION OF THE DRAWINGS

The present disclosure will hereafter be described with reference to the accompanying drawings, wherein like reference numerals denote like elements.

DETAILED DESCRIPTION

Before the present invention is described in further detail, it is to be understood that the invention is not limited to the particular embodiments described. It is also to be understood that the terminology used herein is for the purpose of describing particular embodiments only, and is not intended to be limiting. The scope of the present invention will be limited only by the claims. As used herein, the singular forms "a", "an", and "the" include plural embodiments unless the context clearly dictates otherwise.

It should be apparent to those skilled in the art that many additional modifications beside those already described are possible without departing from the inventive concepts. In interpreting this disclosure, all terms should be interpreted in the broadest possible manner consistent with the context. Variations of the term "comprising" should be interpreted as referring to elements, components, or steps in a non-exclusive manner, so the referenced elements, components, or steps may be combined with other elements, components, or steps that are not expressly referenced. Embodiments referenced as "comprising" certain elements are also contemplated as "consisting essentially of" and "consisting of" those elements.

Brillouin Microscopy

Figure 1A:
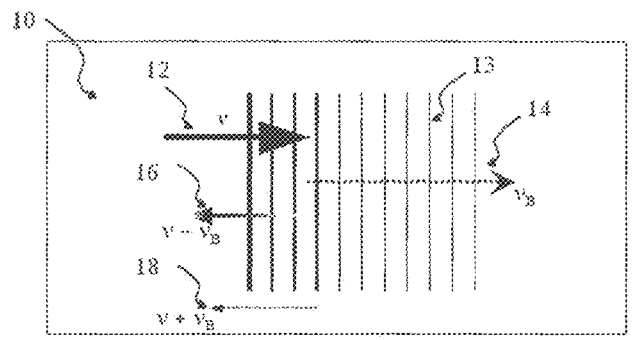
FIG. 1A is a first illustration of an exemplary embodiment of an application and a Brillouin effect of a method according to the present invention.
Figure 1B:
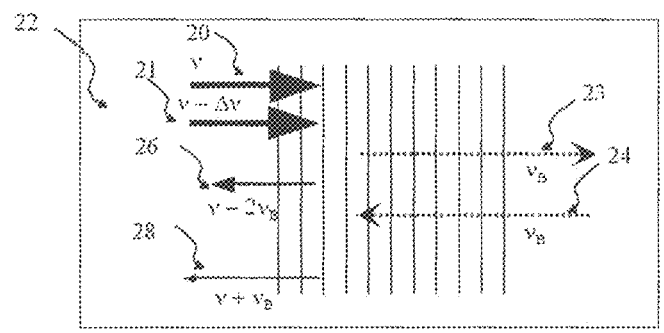
FIG. 1B is a second illustration of an exemplary embodiment of the application and a Brillouin effect of the method according to the present invention.

FIGS. 1A and 1B illustrate exemplary application of an exemplary embodiment of a method which implement a principle of Brillouin scattering according to the present invention. For example, a monochromatic pump light with a frequency $v=\omega/2\pi$ can be provided incident on a medium under test. An exemplary generation of an acoustic wave can be initiated by seed photons which may quantum-mechanically originate from a vacuum fluctuation. There may be one seed photon per unit frequency bandwidth.

The pump and seed photons may interfere with one another, and generate a mechanical stress modulation in the medium via thermal or electrostriction effects. When the stress modulation is phase-matched to one of the characteristic acoustic phonon modes in the medium, the corresponding acoustic phonons can develop efficiently through a coherent process. The excited acoustic phonons in turn may create a refractive-index modulation in the medium, and generate inelastic scattering of photons. The energy and momentum of the photons can be modified by an inelastic scattering procedure. The magnitude of a frequency shift in the scattered photons can be substantially or approximately equal to that of the acoustic phonons. This exemplary procedure is called "Brillouin phenomenon" or "Brillouin scattering." Although both Stokes and anti-Stokes components can be generated, typically Stokes Brillouin component (e.g., frequency down shifted) would likely be predominantly generated.

Exemplary phase matching conditions between the pump scattering light and the acoustic wave can be expressed as:

$$\omega_A = \omega_p - \omega_s \quad (1)$$

$$\vec{k}_A = \vec{k}_p - \vec{k}_s \quad (2)$$

where ω and k are angular frequency and wave number, respectively, and the subscript A, p, and s represent acoustic phonons, pump and scattering (or signal) photons, respectively. The frequency of the phase matched phonons, e.g., the difference between the pump and scattering photons, can be given by $$\omega_A = |\vec{k}_A| V_A = 2V_A |\vec{k}_p| \sin(\theta/2) \qquad (3)$$

where $V_A$ denotes the speed of the acoustic phonon mode (e.g., an acoustic wave) in the medium and θ is an angle between the pump and scattering photons (e.g., optical waves). The Brillouin shift, as expressed in Eq. (3), can increase with the acoustic speed. In a solid state medium, the acoustic speed is proportional to the square root of the modulus. When the two waves propagate at the opposite direction, θ=180.degree., the magnitude of Brillouin shift can become maximum.

For example, FIG. 1A illustrates a backward Brillouin scattering effect in an exemplary implementation of an exemplary embodiment of the present invention. The pump wave 12 with frequency ν is incident on a medium 10, and generates an acoustic wave represented by the wave fronts 13 and its wave vector 14 corresponding to an acoustic frequency $\nu_B$. The Brillouin scattered light 16 satisfying the phase matching condition may have a frequency $\nu-\nu_B$. For example, if there are a large number of acoustic modes present in a sample; then the spectrum of the Brillouin scattered light may consist of multiple lines characterized by their frequencies, magnitudes, and spectral widths, all of which may be related to the mechanical properties of the sample. If the medium 10 is optically transparent, no Anti-stokes Brillouin light 18 with a frequency higher than that of the pump wave would likely be produced. In a turbid medium such as biological tissue, and the light can experience a strong elastic Mie or Rayleigh scattering, in addition to much weaker inelastic Brillouin or Raman scattering. The elastically scattered light, diffused in random directions, may interfere with each other, and can result in a detectable Anti-stokes Brillouin light.

When the acoustic wave is initially provided, the Brillouin phenomenon can be accelerated because of the presence of the scattered light. The scattered light, coherent with the pump light, may amplify the resonant acoustic wave, which in turn may enhance the Brillouin scattering. This positive feedback can result in a strong Brillouin shifted scattered light, e.g., a procedure called "stimulated Brillouin scattering." In a long optical fiber, this exemplary procedure can arise at a very low pump power of several tens of mW, and may be characterized by the Brillouin gain provided by $$g_B(\nu_B) = \frac{2\pi n^7 p_{12}^2}{c\lambda_p^2 \rho_0 v_A \Delta \nu_B} \omega_p - \omega_s \qquad (4)$$

where n is the refractive index, $p_{12}$ is the elasto-optic coefficient, and ρ is the density.

FIG. 1B shows another application of a Brillouin interaction according to the exemplary embodiment of the present invention in a turbid medium 22 initiated by two pump waves 20, 21 with a frequency difference of Δν. The exemplary elastic scattering of the pump waves can stimulate the excitation of acoustic waves (phonons) propagating multiple directions. In the exemplary illustration of FIG. 1B, only two waves propagating along the forward and backward directions 23, 24. The resulting Brillouin scattered light has multiple spectral lines including the Stokes 26 and anti-Stokes 28 components. This exemplary application according to the present invention may be used to enhance the generation of the anti-Stokes line. For example, the maximum Brillouin efficiency can be achieved when the frequency difference substantially matches the frequency of at least one of the acoustic waves (phonons) generated in this manner.

Figure 2:
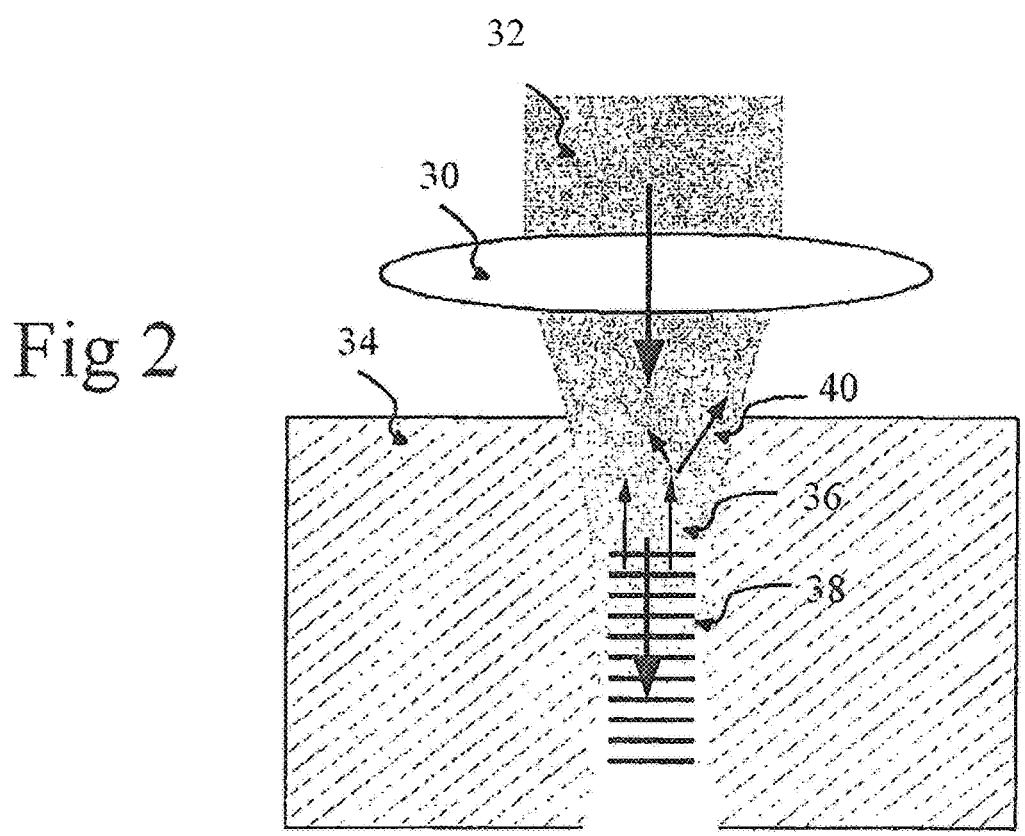
FIG. 2 is an illustration of a Brillouin scattering procedure in tissue using the exemplary embodiment of the method according to the present invention.

Because the efficiency of Brillouin scattering is likely proportional to an optical intensity, a higher efficiency can be obtained by focusing the pump light to the sample. By focusing, higher spatial discrimination or resolution can be obtained. FIG. 2 illustrates an exemplary use of objective lens 30 in accordance with an exemplary embodiment of the present invention for both focusing a pump beam 32 to a sample 34, and collecting a backward propagating Brillouin scattered light 36. Such exemplary detection scheme can be called the "epi configuration." For example, FIG. 2 shows an associated acoustic wave 38 propagating forward, as well as elastically scattered, diffused waves 40. A portion of the elastically scattered light within the numerical aperture of the lens may be also collected. Because the Brillouin process can produce a phase conjugation, the backward Brillouin scattering may be efficiently collected, even with a low numerical-aperture objective lens.

Brillouin spectroscopy is a technique that can measure the spectrum of the Brillouin scattered light, thereby allowing the properties of inherent acoustic phonons of a medium. The Brillouin spectrum may be closely related to the mechanical properties of the medium through the phase matching conditions represented in Equations (1) and (2) (e.g., in their simplest forms).

Figure 3A:
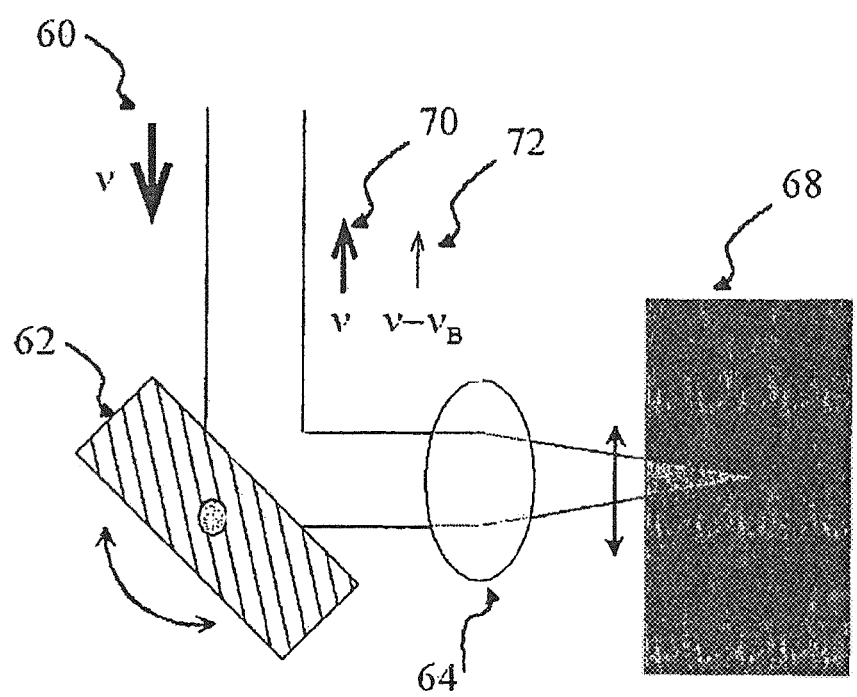
FIG. 3A is a first illustration of a further application of the exemplary embodiment of the method according to the present invention which produces a beam scanning Brillouin imaging.
Figure 3B:
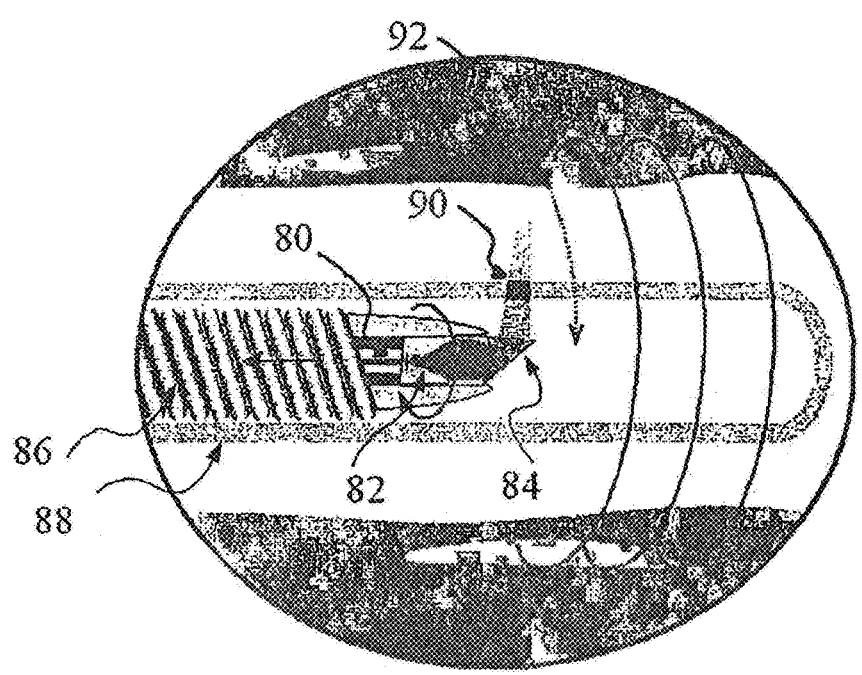
FIG. 3B is a second enlarged illustration of the application of the exemplary embodiment of the method shown in FIG. 3A.

One of the important features of an exemplary embodiment of the present invention is an image generation feature. Using a predetermined or calculated conversion table, the spatial variation of the Brillouin spectra may be presented as an image. To generate images, the pump or probe beam can be scanned laterally across the sample, and/or the sample can itself be translated. FIGS. 3A and 3B illustrate two respective beam scanning applications in accordance with an exemplary embodiment of the present invention which can use a galvanometer and rotational catheter. As shown in FIG. 3A, the pump wave 60 may be reflected by a galvanometer-mounted mirror 62, and focused by an objective lens 64 to a medium 68. Light collected by the objective lens 64 in the epi mode can consist of a backscattered component 70 and a Brillouin shifted component 72. Other conventional scanners can be used, including but not limited to polygonal mirror scanners and MEMS mirrors. FIG. 3B depicts an exemplary beam-scanning application that uses an exemplary embodiment of an arrangement according to the present invention based on a fiber-optic catheter or endoscope for an application to, for example, luminal organ imaging. For example, a catheter can include a single mode fiber 80, a focusing lens 82, a prism 84, a drive shaft 86, and a protective sheath 88. A catheter core, rotated inside the stationary sheath 88, can scan across the tissue 92 using an optical beam 90 in a helical manner.

Figure 4A:
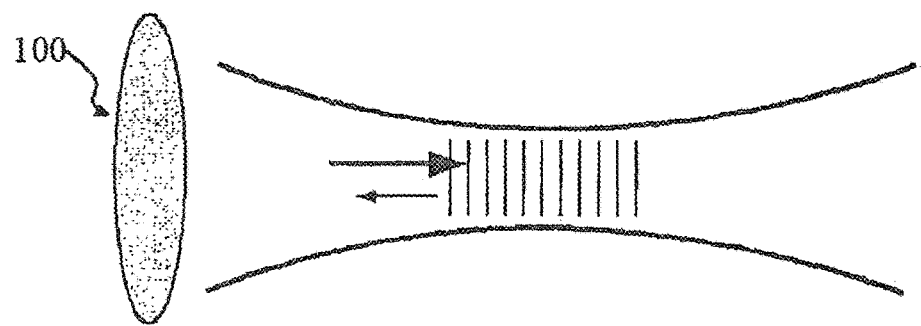
FIG. 4A is a first illustration of a beam focusing procedure implemented by the exemplary embodiment of the method according to the present invention in an exemplary embodiment of an arrangement according to the present invention.
Figure 4B:
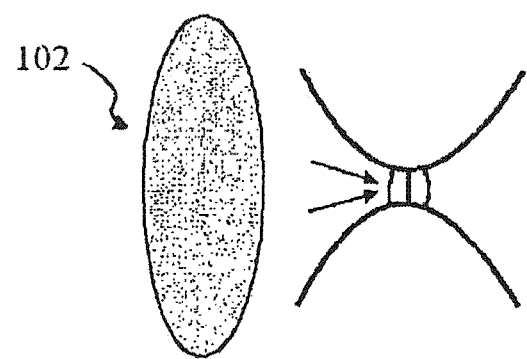
FIG. 4B is a second illustration of a beam focusing procedure implemented by the exemplary embodiment of the method as shown in FIG. 4A.
Figure 4C:
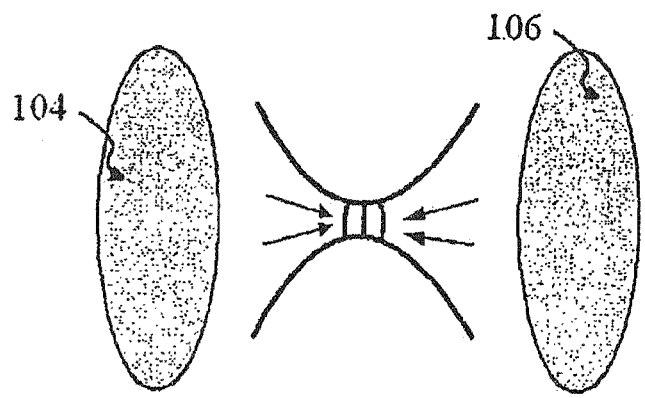
FIG. 4C is a third illustration of a beam focusing procedure implemented by the exemplary embodiment of the method as shown in FIGS. 4A and 4B.

The beam size of the pump beam at the sample can determine the spatial resolution. When a coarse spatial resolution is sufficient, it is possible to use a collimated beam. As shown in FIG. 4A, an exemplary implementation of an objective lens 100 with a low numerical aperture ("NA") can result in a low transverse resolution. With the longitudinal interaction length likely being long and well defined (FIG. 4A); an objective lens 102 with a high NA may provide better transverse and axial resolution, as shown in FIG. 4B. With the high NA, the Brillouin interaction length is likely to be short, and the phase matching can be met over a large solid angle. In both cases, the backward-propagating Brillouin light may be detected in the epi configuration. FIG. 4C depicts another exemplary implementation an use of the exemplary embodiments of the method and arrangement according to the present invention using at leas two objective lenses 104, 106. This scheme, however, may not be appropriate for thick tissue or in vivo applications.

Figure 5:
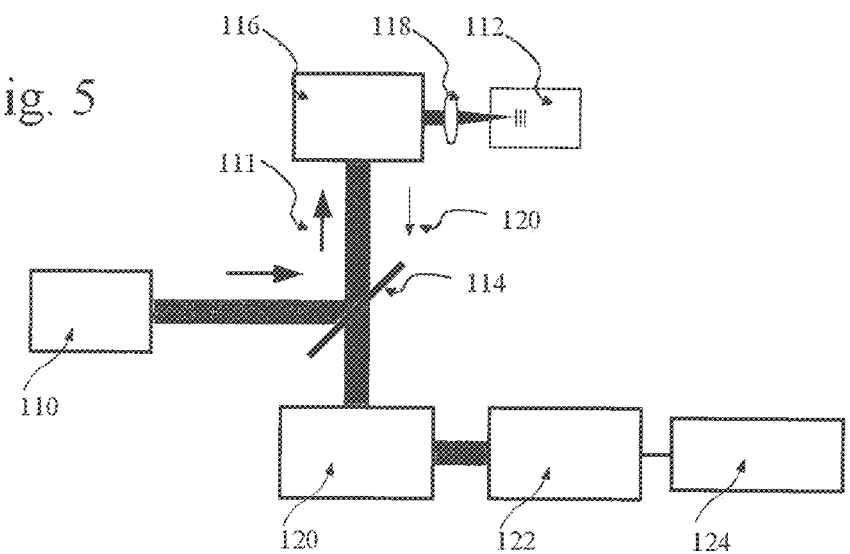
FIG. 5 is a block diagram of an exemplary embodiment of a scanning-beam Brillouin spectroscopy arrangement in accordance with the present invention.

FIG. 5 depicts a block diagram of an exemplary embodiment of an arrangement according to the present invention. For example, the arrangement of FIG. 5 includes a light source 110, preferably a monochromatic laser emitting visible or infrared light source, and a pump beam/wave 111 that can be illuminated to a sample 112 through a beam splitter 114, a beam scanner 116, and an objective lens 118. The light source 110 can be, but not limited to, a cw single frequency laser with a center wavelength between 0.5 and 1.8 microns and a narrow line width, typically less than 100 MHz, providing temporal coherence longer than the lifetime of phonons. Another preferred type of light source is a Q-switched single frequency laser. The pulse repetition rate may range from 1 to 100 kHz, and the pulse duration from 10 ns to 1 μs. The Q-switched pump light can result in higher Brillouin generation efficiency because the intensity is higher than that of cw light at the same average power level. The light source 110 may utilize or include an optical arrangement to deliver more than one frequency components (illustrated in FIGS. 8A and 8B). The lateral step size of the beam scan can be approximately equal to the focal spot size of the pump beam/wave 111 in the sample 112.

The scattered light 120 provided from the sample 112 and collected by the objective lens 118 may originate from both elastic and inelastic scattering. The spectrum of the scattered light may be measured using a spectrally-selective arrangement 120, such as scanning filters, etalons, virtual interferometer phase arrays, or spectrometers. Various scanning filters are known in the art, including but not limited to a Fabry-Perot interferometer. For example, the Brillouin shift can be as high as several tens of GHz. The exemplary Fabry-Perot scanning interferometer may have a free spectral range of 50 GHz, and finesse of 1000. The spectrally selected optical photons may then be converted to electrical signals at a detector 122 (e.g., a photo-multiplier tube, avalanche photodiode, or charge-coupled-device array).

Figure 6A:
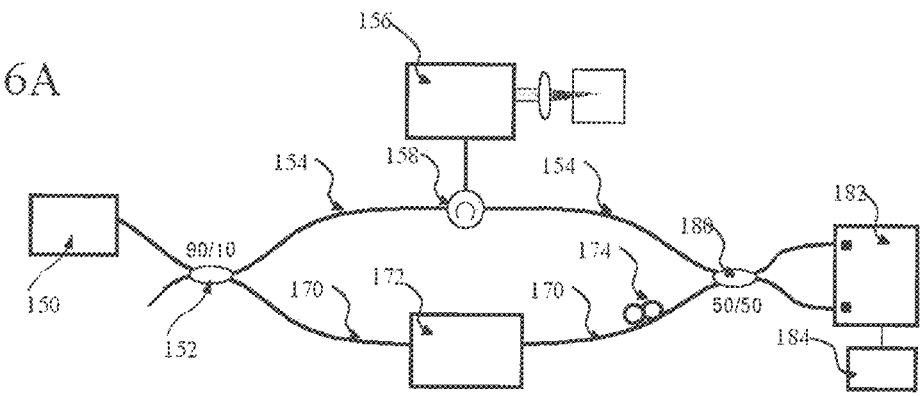
FIG. 6A is a block diagram of a first exemplary embodiment of a Brillouin microscopy arrangement that can use interferometry in accordance with the present invention.
Figure 6B:
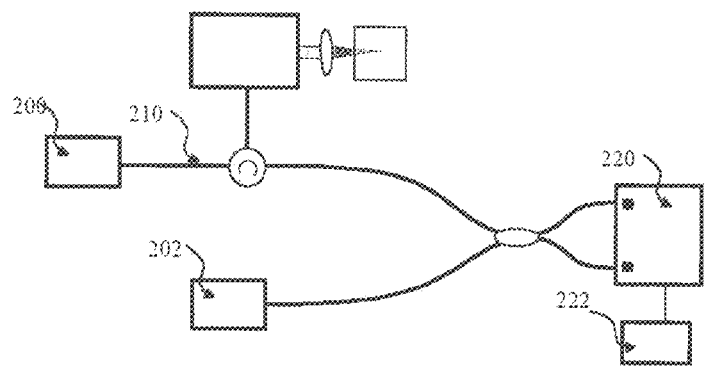
FIG. 6B is a block diagram of a second exemplary embodiment of the Brillouin microscopy arrangement that can use interferometry in accordance with the present invention.

Other exemplary embodiments of the present invention that use fiber-optic heterodyne interferometers are shown in the block diagrams of FIGS. 6A and 6B. In FIG. 6A, a single-frequency laser 150 is shown to be coupled to a fiber-optic beam splitter 152 with an exemplary splitting ratio of approximately 90:10. One optical path, termed a sample arm 154, can be connected to a beam scanner 156 via a circulator 158, and the other path, termed a reference arm 170, may contain a frequency shifter 172 such as an acousto-optic or electro-optic modulator. Both the sample and reference arms 154, 170 may be combined at another fiber-optic beam splitter 180, with, e.g., equal splitting ratios. The interference signal between the backscattered light in the sample arm 154 and the frequency-shifted reference light in the reference arm 170 can be measured by a dual balanced receiver 182, and processed using a computer 184. The frequency shifter 172 can be used to decrease the beat frequency between scattered and reference light, and a polarization controller 174 may also be utilized, as shown in FIG. 6A. According to another exemplary embodiment of the present invention, an electrical spectrum analyzer may replace or complement the computer 184. Alternatively, the Brillouin spectra may be determined by tuning the magnitude of frequency shift by the shifter 172 and measuring the beat signal with a low-bandwidth detector 182.

FIG. 6B depicts a block diagram of another exemplary configuration according to a further exemplary embodiment of the present invention that uses two monochromatic lasers 200, 202, with a tunable frequency difference. One laser 200 is coupled to a sample arm 210 for delivering the pump wave. The second laser 202 can serve as a local oscillator to provide the reference light with a frequency detuned from that of the pump source by a predetermined amount. The frequency of the local oscillator can be close to that of one of Brillouin signal light, and the beat frequency may be measured by a detector 220. For example, the line widths of the pump source 200 and the local oscillator 202 should be significantly narrow, and typically less than 100 kHz, to effect a temporal coherency between the scattered and reference light.

Figure 6C:
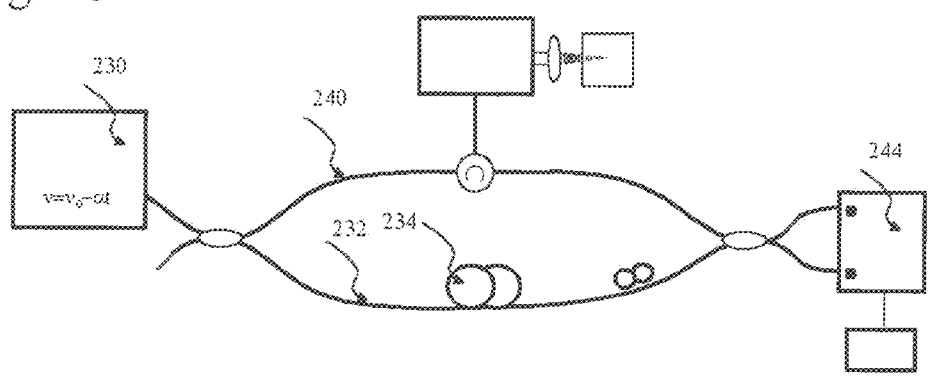
FIG. 6C is a block diagram of a third exemplary embodiment of the Brillouin microscopy arrangement that can use interferometry in accordance with the present invention.

FIG. 6C illustrates a block diagram of yet another exemplary embodiment of the arrangement according to the present invention based on a frequency-swept laser 230 that can be preferably either one of a mode-hop-free extended-cavity semiconductor laser, temperature-tuned distributed feedback laser, and cavity-modulated solid-state laser. The reference arm 232 may contain a delay line 234 providing an optical delay by a fixed amount and/or a variable amount controlled by the length difference between the reference and sample arms 232, 240. The length mismatch between the two arms can be selected as follows:

$$\Delta L \approx \frac{c}{n\alpha} v_B \qquad (5)$$

where c is the speed of light, n is the refractive index of medium, .alpha. is the tuning speed, and $v_B$ is the frequency of acoustic phonons of interest. Pursuant to such selection, the electrical beat frequency measured by a detector 244 can be significantly smaller than the acoustic frequency. On the other hand, when the path lengths of the two arms 232, 240 are substantially matched, such exemplary measurement technique may be similar to the optical frequency domain reflectometry. The interference signal measured as a function of wavelength can be processed via a Fourier transform to produce an axial profile of elastic backscattering coefficients. Similarly, with appropriate length mismatch, similar signal processing may yield an axial profile of Brillouin scattering coefficients.

Figure 7A:
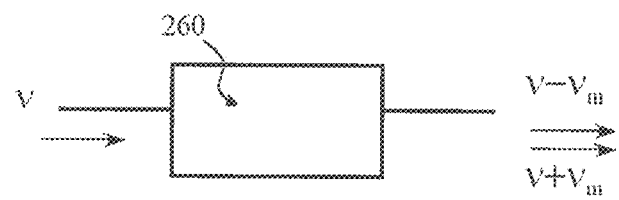
FIG. 7A is an illustration of a first stage in generating an exemplary two-frequency pump wave using an exemplary embodiment of a method and arrangement in accordance with the present invention.
Figure 7B:
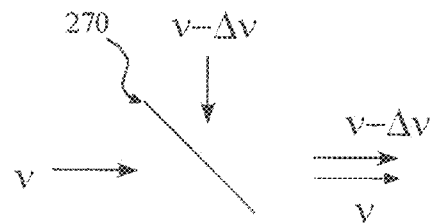
FIG. 7B is an illustration of a second stage in generating the exemplary two-frequency pump wave in conjunction with the generation shown in FIG. 7A.
Figure 7C:
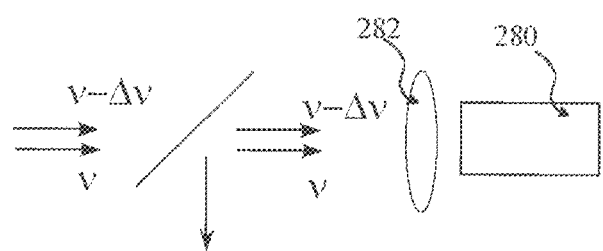
FIG. 7C is an illustration of a third stage in generating the exemplary two-frequency pump wave in conjunction with the generation shown in FIGS. 7A and 7B.
Figure 7D:
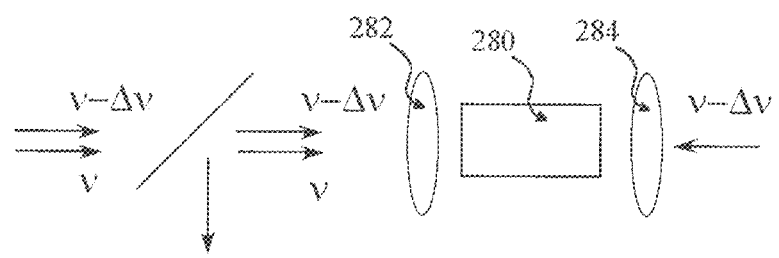
FIG. 7D an illustration of is a fourth stage in generating the exemplary two-frequency pump wave in conjunction with the generation shown in FIGS. 7A-7C.

FIGS. 7A-7D depict various stages of two different exemplary source arrangements according to an exemplary embodiment of the present invention which are capable of producing the pump wave consisting of two different frequency components. The Brillouin spectroscopy based on such two-frequency pump wave is illustrated in FIG. 1B and described herein above. For example, in FIG. 7A, an electro-optic modulator with a proper DC bias can produce two sidebands from a monochromatic laser input. In FIG. 7B, two low-drift monochromatic lasers may be combined with a beam combiner 270. In the epi configuration, the combined pump waves may be delivered to a sample 280 through an objective lens 282, as shown in FIG. 7C. In a transmission configuration, a secondary objective lens 284 may be used to launch one of the two frequency components in the opposite direction, as shown in FIG. 7D.

Figure 8A:
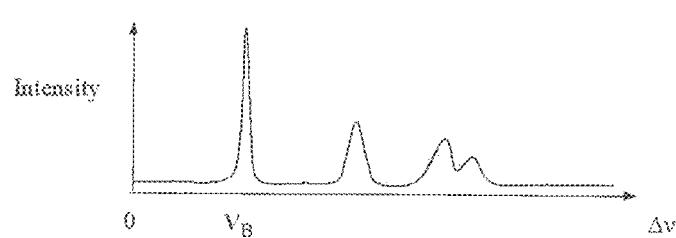
FIG. 8A is a first exemplary illustration of a Brillouin signal generation using the exemplary embodiment of the method and arrangement in accordance with the present invention.
Figure 8B:
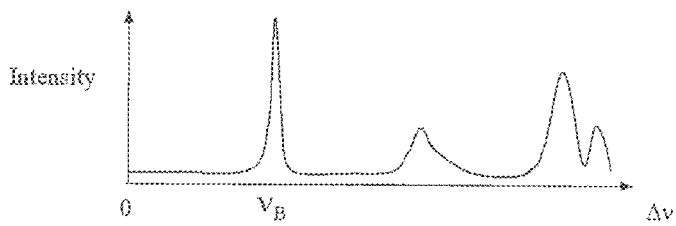
FIG. 8B is a second exemplary illustration of the Brillouin signal generation using the exemplary embodiment of the method and arrangement in accordance with the present invention.
Figure 8C:
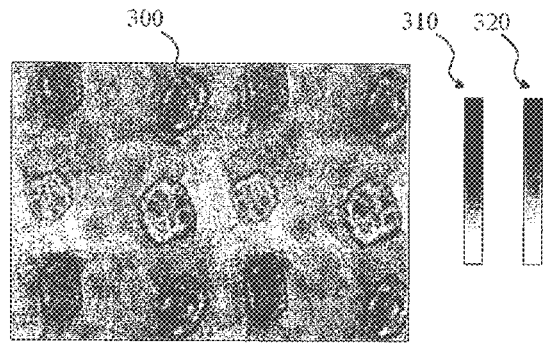
FIG. 8C is an illustration of an image produced by the signals shown in FIGS. 8A and 8B using the exemplary embodiment of the method and arrangement in accordance with the present invention.

FIGS. 8A and 8B illustrate exemplary Brillouin spectra obtained from two different locations in a sample according to the exemplary embodiment of the present invention. For example, the difference between the two spectra, represented in these figures by the magnitude of $v_B$, may indicate a difference in stiffness between the two locations. An image 300 (shown in FIG. 8C) can be formed based on the measured Brillouin signal and by using a grayscale look up table 310 and/or a false color lookup table 320. The lookup table(s) 310, 320 may be based on the magnitude and/or the frequency of one or more specific Brillouin peaks.

Figure 9A:
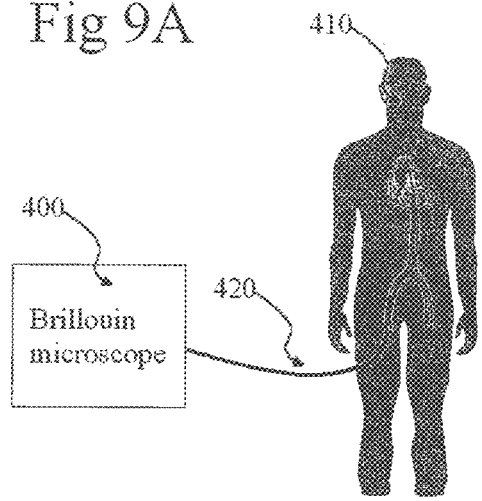
FIG. 9A is an illustration of a medical application using an exemplary embodiment of a catheter in accordance with the present invention.
Figure 9B:
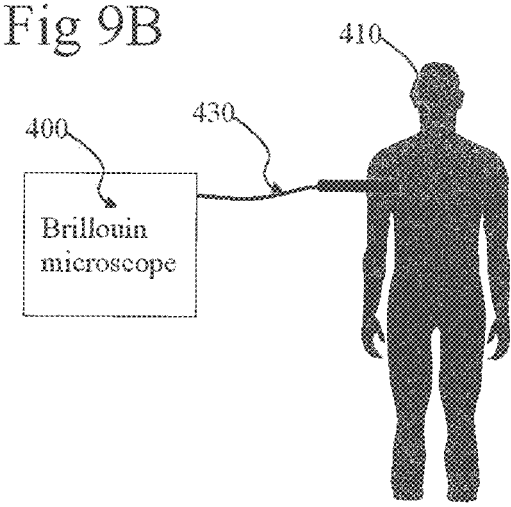
FIG. 9B is an illustration of a medical application using an exemplary embodiment of an endoscope in accordance with the present invention.

FIGS. 9A and 9B illustrates possible exemplary clinical applications of Brillouin microscopy 400 in human 410 by use of a fiber-optic catheter 420 or endoscope 430 in accordance with an exemplary embodiment of the present invention. The catheter 420 may have a similar configuration as shown in FIG. 3B. and described above The endoscope 430 may employ a two-axis XY beam scanning actuator, such as MEMS scanners. Potential applications of Brillouin microscopy can include tissue characterization based on biomechanical properties, cancer diagnosis, tumor margin determination, wound healing monitoring, tissue ablation monitoring, and tissue engineering among many.

The foregoing merely illustrates the principles of the invention. Various modifications and alterations to the described embodiments will be apparent to those skilled in the art in view of the teachings herein. Indeed, the arrangements, systems and methods according to the exemplary embodiments of the present invention can be used with any OCT system, OFDI system, spectral domain OCT (SD-OCT) system or other imaging systems, and for example with those described in International Patent Application PCT/US2004/029148, filed Sep. 8, 2004, U.S. patent application Ser. No. 11/266,779, filed Nov. 2, 2005, and U.S. patent application Ser. No. 10/501,276, filed Jul. 9, 2004, the disclosures of which are incorporated by reference herein in their entireties. It will thus be appreciated that those skilled in the art will be able to devise numerous systems, arrangements and methods which, although not explicitly shown or described herein, embody the principles of the invention and are thus within the spirit and scope of the present invention. In addition, to the extent that the prior art knowledge has not been explicitly incorporated by reference herein above, it is explicitly being incorporated herein in its entirety. All publications referenced herein above are incorporated herein by reference in their entireties.

In one exemplary embodiment of the present invention, a pump beam can be scanned over the biological sample through an objective lens, and the beating signal between the pump and Brillouin-shifted optical waves may be detected to characterize the Brillouin spectrum. The measured spectral features of the Brillouin signal can be converted to an image, e.g., by use of a proper lookup table or computer software which associates the spectral features to data associated with images. For example, thin cross-sectional images of a thick biological sample can be obtained by using a high numerical-aperture objective lens and confocal detection.

According to another exemplary embodiment of the present invention, a secondary pump beam with a different optical frequency can be used to facilitate a generation of acoustic phonons through stimulated or forced Brillouin scattering. In an exemplary variant of the present invention, anti-stokes Brillouin scattering technique(s) can be implemented using multiple pump beams. Various pump and probe techniques, and/or heterodyne or spectrometer-based detection techniques can be used.

Tissue biomechanical properties can be altered in a variety of disease states, and therefore may be appropriate targets for non-invasive diagnosis. A further exemplary embodiment of the systems, arrangements and processes of the present invention can make it possible to obtain the information about intrinsic tissue biomechanical properties that are not readily available by other ways, and therefore determine a wide range of applications in biology and medicine. For example, the Brillouin microscopy can become a clinical tool for the detection of early-stage cancers or intra-operative determination of tumor margins. Considering that tumors are generally stiffer than surrounding healthy tissue, the Brillouin spectrum of a tumor can possibly exhibit a stronger magnitude at high frequencies than that of normal tissues. Atherosclerosis is another medical area the Brillouin microscopy may be useful for characterizing stress and tissue compliance to identify plaques at risk for causing an acute coronary event. For example, a scanning catheter or hand-held endoscope may be used to perform the Brillouin measurement in living patients.

Thus, in accordance with one exemplary embodiment of the present invention, arrangements and methods are provided for obtaining information associated with an anatomical sample. For example, at least one first electro-magnetic radiation can be provided to the anatomical sample so as to generate at least one acoustic wave in the anatomical sample. At least one second electro-magnetic radiation can be produced based on the acoustic wave. At least one portion of at least one second electro-magnetic radiation can be provided so as to determine information associated with at least one portion of the anatomical sample.

According to another exemplary embodiment of the present invention, the information based on data associated with the second electro-magnetic radiation can be analyzed. The first electro-magnetic radiation may include at least one first magnitude and at least one first frequency. The second electro-magnetic radiation can include at least one second magnitude and at least one second frequency. The data may relate to a first difference between the first and second magnitudes and/or a second difference between the first and second frequencies. The second difference may be approximately between −100 GHz and 100 GHz, excluding zero.

In another exemplary embodiment of the present invention, at least one fourth arrangement configured to image the portion of the anatomical sample based on data associated with the second electro-magnetic radiation can be provided. Further, at least one fifth arrangement configured may be provided to translate the at least one electro-magnetic radiation across the anatomical sample. The fifth arrangement may include at least one lens, and the lens can focus the first electro-magnetic radiation and can collect the second electro-magnetic radiation. The second arrangement can include a spectral filter which may facilitate a determination of a spectrum of the second electro-magnetic radiation. The information can be associated with a biomechanical property of the anatomical sample. The anatomical sample may be a living subject.

According to still another exemplary embodiment of the present invention, the first electromagnetic radiation may have a center wavelength which is approximately between 0.5-1.8 μm. The first electromagnetic radiation can have a line width which is smaller than approximately 100 MHz. The first electromagnetic radiation can have a form of a plurality of pulses, and the duration of each of the pulses may be longer than approximately 10 ns. The first electromagnetic radiation can also include at least two first electromagnetic radiations, a first one of the first electro-magnetic radiations possibly having a first frequency, and a second one of the first electro-magnetic radiations possibly having a second frequency. A difference between the first and second frequencies may be between approximately zero and 100 GHz. It is possible to receive at least one third electromagnetic radiation which has at least one third magnitude and at least one third frequency. The second frequency may be determined as a function of the first and third frequencies. The third electro-magnetic radiation can be forwarded from an electromagnetic radiation source.

Brillouin Microscopy with Improved Axial Location Information

As discussed above, a need exists to improve the measurement of z-coordinate or axial direction measurements in Brillouin microscopy systems and methods. This disclosure provides systems and methods for achieving this desired result.

As used herein, "z-coordinate" or "axial" refers to a direction of propagation of a Brillouin probe beam. An "axial depth" refers to a distance along the axial direction relative to a landmark (for example, relative to a corneal epithelium). An "arm" refers to an optical beam path. A "beam" refers to an optical signal that is directed, steered, guided, or otherwise utilized in the systems and methods described herein.

This disclosure provides systems and methods for conducting Brillouin microscopy, and in particular conducting an axial Brillouin scan, with a co-registered three-dimensional imaging modality. The three-dimensional imaging modality can provide information regarding the location of the focal point of the Brillouin probe beam, which can be used to either map the resulting measurements to specific locations or to position the Brillouin probe beam in a desired location for measurement. The result of this co-registration is a technique that is capable of providing accurate axial scans for Brillouin mapping, capable of overcoming movement of the medium that is being analyzed (for example, movement of an eye whose cornea is being analyzed), and capable of quickly and relatively easily perform reliable Brillouin mapping. The accurate axial scans allow three-dimensional mapping having improved quality. The capability to account for movement is achieved by sensing the movement with the three-dimensional imaging modality, and then re-registering the location of the focal point of the Brillouin probe beam. Accounting for movement such as this is important when working with patients who can often struggle to remain still during a procedure. The speed and relative ease of the methods described herein suggest potential widespread adoption of the techniques.

This disclosure provides a system for acquiring Brillouin maps with improved determination of the axial depth of the focus of the Brillouin probe beam. The system can include a Brillouin microscope, a three-dimensional imaging modality with a imaging sample beam that is co-registered and/or multiplexed with a Brillouin probe beam of the Brillouin microscope, and a multiplexed probe fixture that can manipulate the co-registered and/or multiplexed Brillouin probe beam and imaging sample beam.

Figure 10:
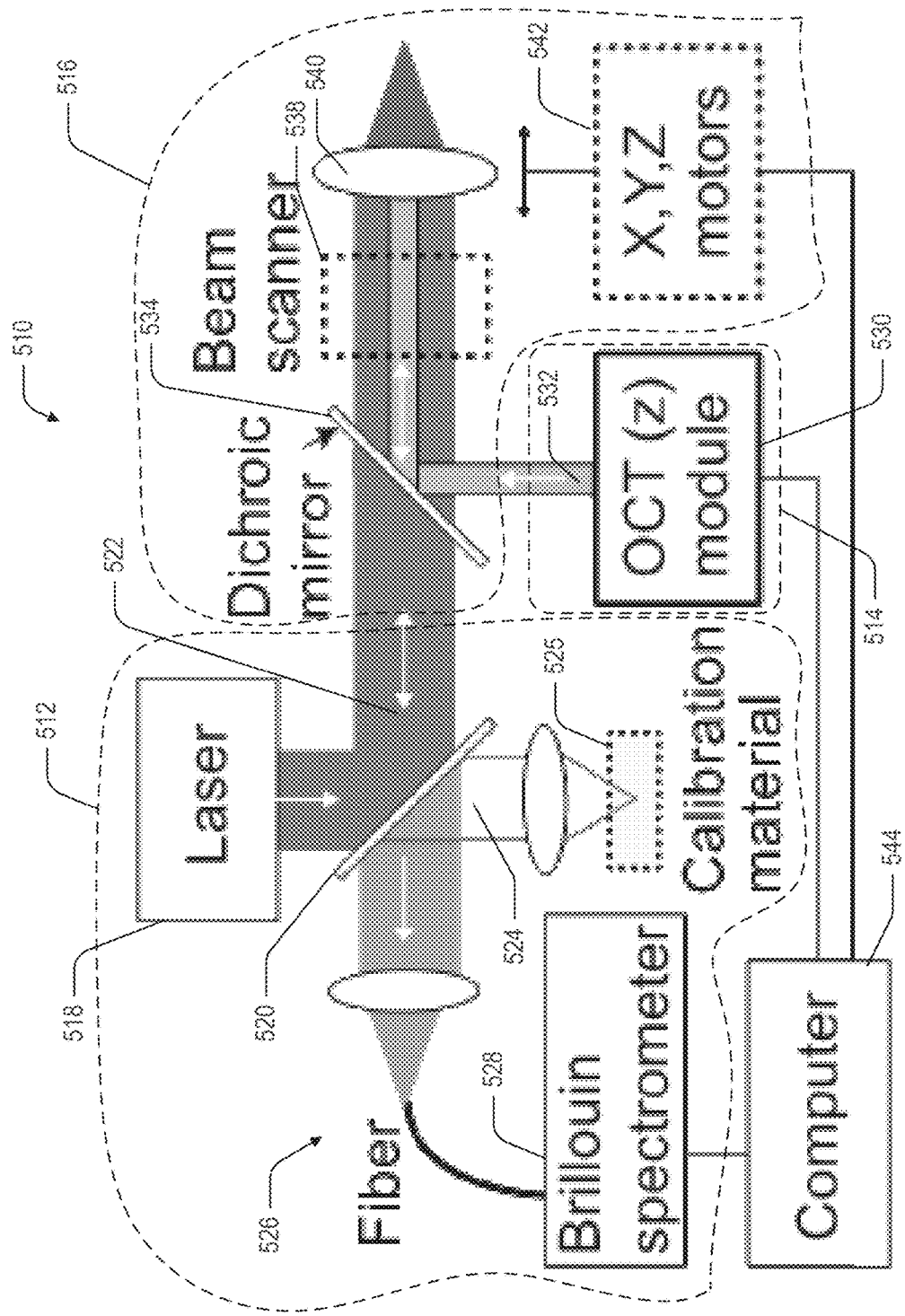
FIG. 10 is a schematic illustration of an optical system, in accordance with an aspect of the present disclosure.

Referring to FIG. 10, a system 510 for acquiring Brillouin maps of a medium with improved determination of the axial depth of the focus of the Brillouin probe beam is illustrated in schematic form. The system 510 includes an optical coherence tomography (OCT) system as the three-dimensional imaging modality. The system 510 can include a Brillouin microscope 512, an optical coherence tomography (OCT) system 514, and a multiplexed probe fixture 516.

The Brillouin microscope 512 can include a Brillouin light source 518, an optical beamsplitter 520, a Brillouin probe arm 522, a Brillouin reference arm 524, a Brillouin spectrometer optical path 526, and a Brillouin spectrometer 528. In use, the Brillouin light source 518 emits light that travels to the optical beamsplitter 520. A portion of the light is reflected by the optical beamsplitter 520, and that portion, which shall be referred to as the Brillouin probe beam, travels along the Brillouin probe arm 522.

The Brillouin light source 518 can be the same type of light source as described above with respect to the light source 110. The Brillouin microscope 512 can include any of the features of the arrangements described above. The optical beamsplitter 520 can be substituted for any suitable optics that can direct the light in the fashion described.

The Brillouin reference arm 524 can include a Brillouin reference material 525. The Brillouin reference material 525 can be used for frequency calibration of the Brillouin signals. In some aspects, two or more Brillouin reference materials 525 can be used. Brillouin reference materials 525 have their frequency shifts pre-determined as a function of ambient temperature. The system 510 can also include a temperature sensor (not illustrated) for determining the frequency shift of the Brillouin reference material 525. A motorized shutter (not illustrated) can selectively block the Brillouin probe arm 522 or the Brillouin reference arm 524. By blocking the Brillouin probe arm 522 and not blocking the Brillouin reference arm 524, a reference measurement can be acquired before or after a Brillouin measurement is acquired. By blocking the Brillouin reference arm 524 and not blocking the Brillouin probe arm 522, the Brillouin measurement can be acquired. The Brillouin reference material can be a material selected from the group consisting of a glass, a plastic, water, and combinations thereof. The Brillouin reference material can be polymethyl methacrylate or water.

The OCT system 514 can include an OCT module 530 including an OCT sample arm 532.

The multiplexed probe fixture 516 can include a selectively reflective mirror 534 (for example, a dichroic mirror) that is responsible for multiplexing the Brillouin probe arm 522 and the OCT sample arm 532 to provide a multiplexed probe arm 536 and is also responsible for separating returning Brillouin and OCT signals. The multiplexed probe fixture 516 can further include a beam scanner 538 that provides x- and y-coordinate translation of the multiplexed probe arm 536, a lens system 540 (such as an objective lens, but including any suitable lens arrangement known to a person having ordinary skill in the art to be suitable for use with optical systems such as those described herein) that provides z-coordinate translation of a focal point of the multiplexed probe arm 536, and one or more motors 542 configured to provide spatial control of the beam scanner 538 and the lens system 540.

The system 510 can further include a computer 544 to control the one or more motors 542, to receive data from the Brillouin spectrometer 528 and the OCT module 530, and to further control the system 510 or analyze data as a person having ordinary skill in the art would appreciate. The system 510 can also include any necessary wired or wireless data connections so as to facilitate functioning of the system.

The OCT module 530 can include any OCT arrangement known to a person having ordinary skill in the art to be suitable for providing the axial positioning information discussed herein. For example, the OCT module 530 can include a swept source optical frequency domain (OFDI) system, a spectral domain optical coherence tomography (SD-OCT) system, and the like.

Figure 11:
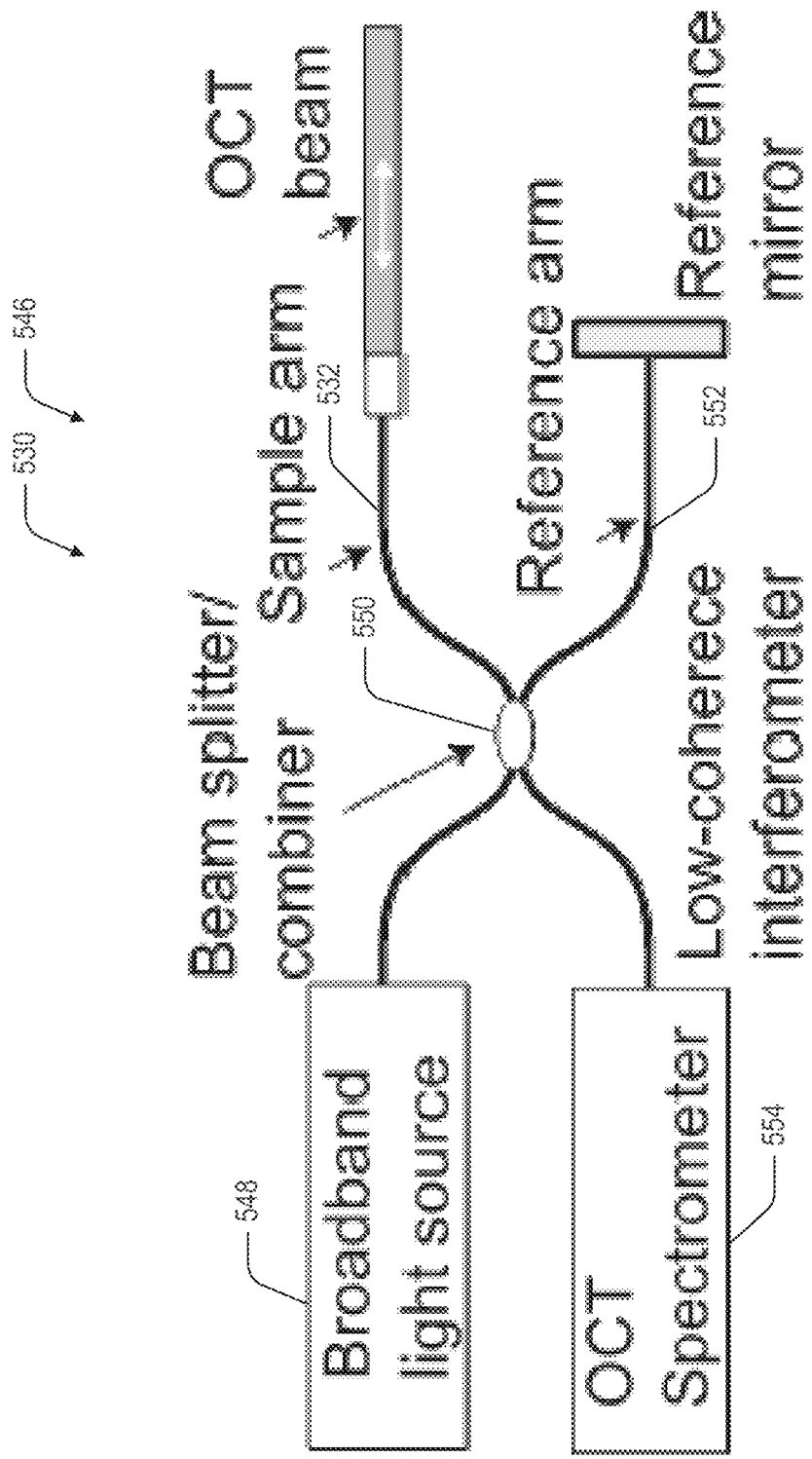
FIG. 11 is a schematic illustration of an optical coherence tomography (OCT) module, in accordance with an aspect of the present disclosure.

Referring to FIG. 11, an OCT module 530 in the form of a SD-OCT system 546 is illustrated in schematic form. The SD-OCT system 546 can include an OCT light source 548, a beam splitter/combiner 550, the OCT sample arm 532, an OCT reference arm 552, and an OCT spectrometer 554.

The OCT light source 548 can be a wavelength-swept source or a broadband source, depending on the particular OCT technique that is desired. A person having ordinary skill in the art will appreciate the circumstances under which each is appropriate. The OCT light source 548 can be a light emitting diode (LED), a super luminescent diode (SLD), a laser, or other light sources known to those having ordinary skill in the art to be suitable for use in OCT systems.

The OCT spectrometer 554 can include a diffractive optical element, such as a diffraction grating, and a camera, such as a charge-coupled device. The OCT spectrometer 554 can include a photo-detector, such as a photodiode, to detect an interference signal between the sample- and reference-arm light.

The Brillouin reference arm 524 and the OCT reference arm 552 can be reflective or transmissive type reference arms.

The system 510 can be configured with fiber-optical, integrated optic, or free space components as optical beam paths.

The computer 544 can have stored on it software that controls the one or more motors 542. The computer 544 can have stored on it software to generate A-line images from the OCT signals. The control of the one or more motors 542 can be in response to an OCT signal or in response to the A-line images. The computer 544 can have stored on it software to co-register the OCT images with the acquired Brillouin signals to generate a Brillouin map. The computer 544 can have stored on it software to interpret the Brillouin signals to provide a mechanical property that corresponds to the measured Brillouin signals. The computer 544 can have stored on it software to generate mechanical property maps utilizing the interpreted mechanical properties and the Brillouin map.

Figure 12:
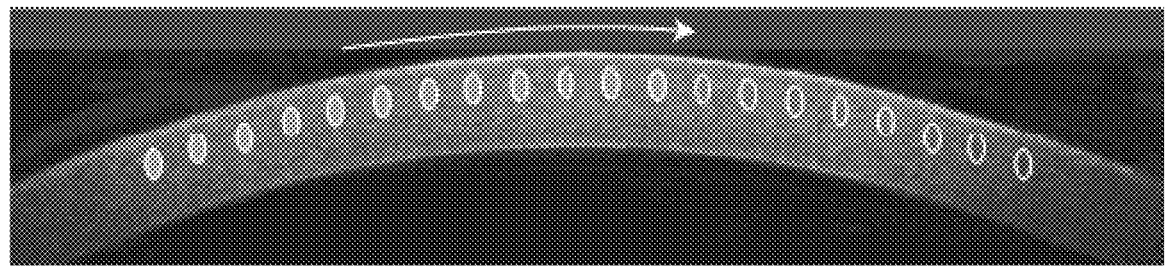
FIG. 12 is a schematic representation of transverse, two-dimensional imaging of a cornea, in accordance with an aspect of the present disclosure.
Figure 13:
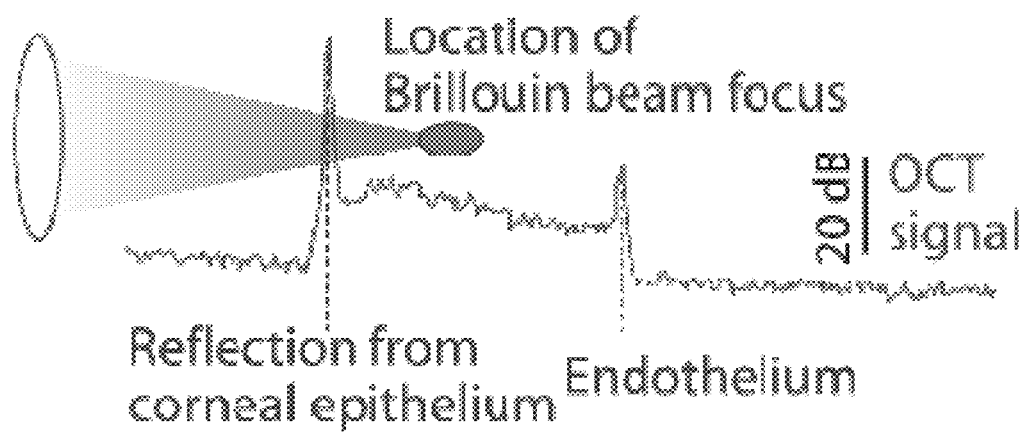
FIG. 13 is an OCT signal showing reflections from a corneal epithelium and endothelium and illustrated with a Brillouin beam focus.

In one exemplary aspect of the disclosure using a system 510 as illustrated in FIGS. 10 and 11, the system 510 can be used to measure mechanical properties of an eye. The system 510 can include a single-frequency semiconductor laser operating at near infrared wavelengths (e.g., 700-810 nm) operating at a power that delivers 1-30 mW to the cornea, which is lower than the power levels at which damage can occur in the cornea, as the Brillouin light source 518. An OCT module 530 can be a spectral-domain OCT module including an interferometer (e.g., the beam splitter/combiner and the various beam paths/arms) an OCT spectrometer 554, and a broadband light source 548. The broadband light source 548 can be a LED or SLD in a spectral range of 820-900 nm operating at a power that delivers 0.5-0.8 µW to the cornea. The OCT spectrometer 554 can include a diffraction grating and a CCD camera. The OCT sample arm beam can be combined with and separated from a 780-nm Brillouin probe beam by a dichroic beam splitter. The sample arm light can be returned from the tissue and combined with a reference light returning from the OCT reference arm 552, and the spectra interference signal can be recorded by the CCD. The output of the CCD can be analyzed in the computer 544 using data processing methods known to a person having ordinary skill in the art, including but not limited to, data processing that involves a Fourier transform. Software on the computer 544 can generate A-line images and control xyz-motors or a xyz beam scanner in real time with a delay of less than 10 ms. From these A-line images, the axial position of the focus of the Brillouin probe beam can be readily determined. This information can be used to contrast an axial Brillouin profile with accurate depth registration. This can facilitate 3-dimensional imaging. OCT can also enable transverse, two-dimensional imaging, as illustrated in FIG. 12. As the Brillouin beam is moved to a next lateral position, OCT can provide real-time depth information and control the motor or scanner to place the focus of the Brillouin beam to a desired axial location. Referring to FIG. 13, an OCT signal is shown with an illustrated Brillouin beam focus to illustrate the real-time information on the location of the cornea with respect to the beam focus that is provided by the OCT system.

Figure 14:
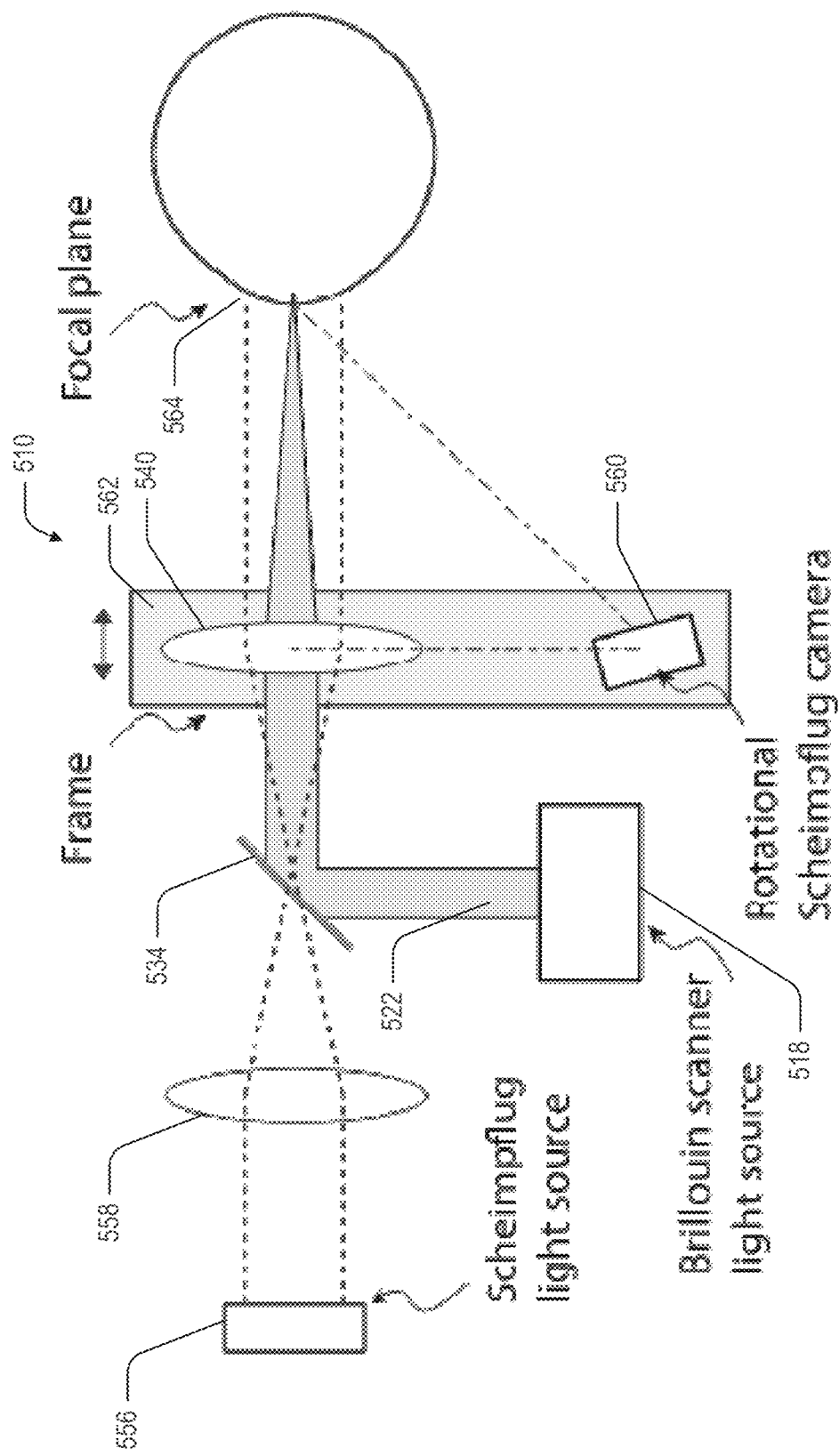
FIG. 14 is a schematic illustration of an optical system, in accordance with an aspect of the present disclosure.

Referring to FIG. 14, a system 510 for acquiring Brillouin maps of a medium with improved determination of the axial depth of the focus of the Brillouin probe beam is illustrated in schematic form. The system 510 includes a Scheimpflug camera system as the three-dimensional imaging modality. The system 510 can include a Brillouin microscope 512 including a Brillouin light source 518 and a Brillouin probe arm 522, a Scheimpflug light source 556, a Scheimpflug lens 558, a selectively reflective mirror 534, a beam scanner (not illustrated), a lens system 540, a Scheimpflug camera 560, a frame 562 that is translatable along the z-direction to move the lens system 540 and the Scheimpflug camera 560 along the z-direction, and one or more motors (not illustrated) configured to provide spatial control of the beam scanner and the frame 562.

The Scheimpflug light source 556 can be a slit light source that is image onto a focal plane through the Scheimpflug lens 558 and the lens system 540. The focal plane 564, which is configured to coincide with the focal point of the Brillouin probe beam, is imaged by the Scheimpflug camera 560. The Scheimpflug camera 560 is configured to rotate about the optical axis of the imaging system. A Scheimpflug image that is acquired can display the cross-section of the medium, such as a cornea and/or lens, and its depth location is registered with respect to the focal plane, the center of which corresponds to the focal point of the Brillouin optical beam. The Scheimpflug image can provide real-time feedback to control scanning of the focal point of the Brillouin probe beam across the sample.

Figure 15:
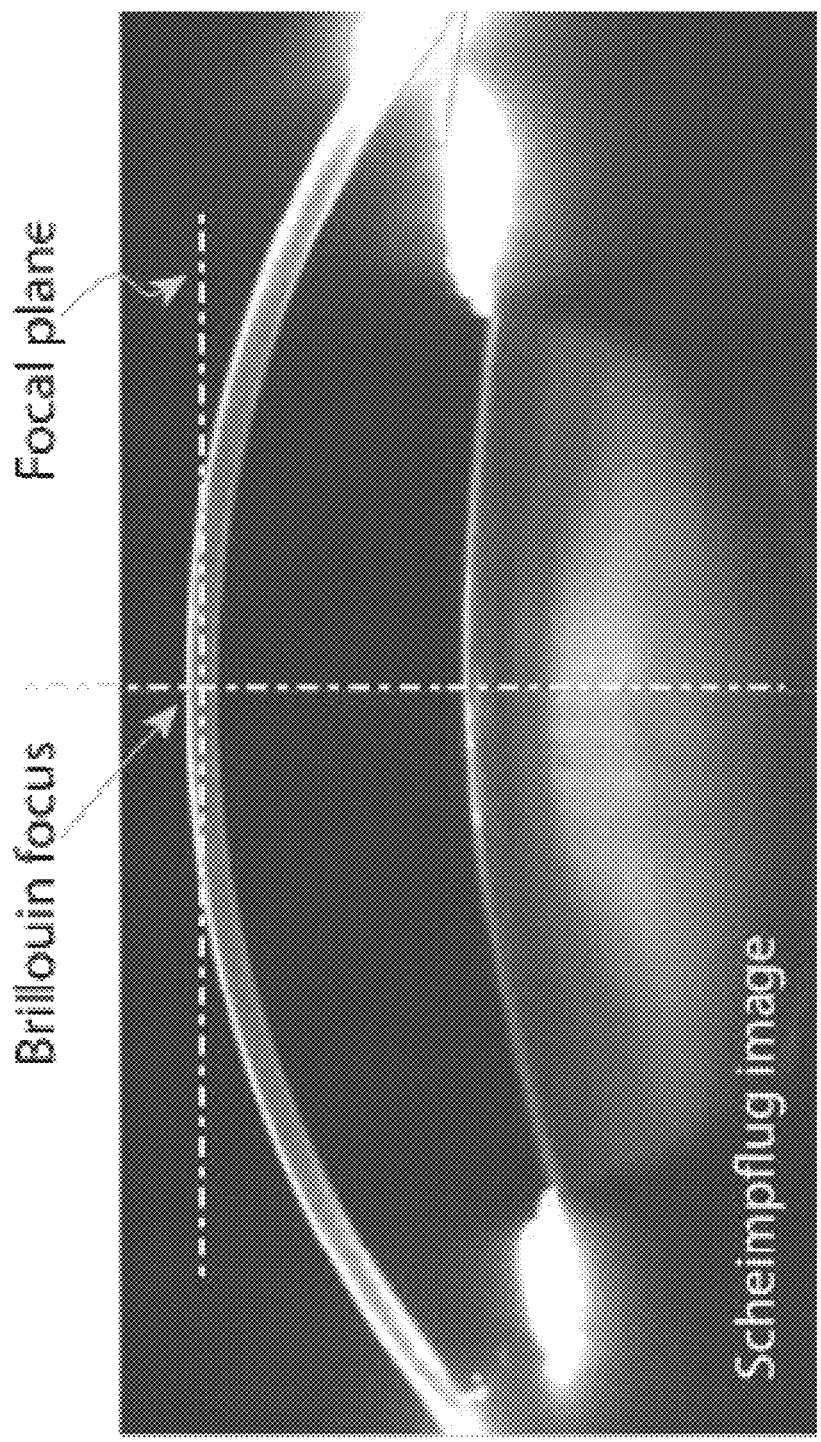
FIG. 15 is a Scheimpflug image showing the relationship between the image plane of the Scheimpflug sample beam and the Brillouin probe beam focal point.

Referring to FIG. 15, a representative Scheimpflug image is shown illustrating the spatial relationship between the focus of the Brillouin probe beam and the focal plane of the Scheimpflug sample beam.

Figure 16:
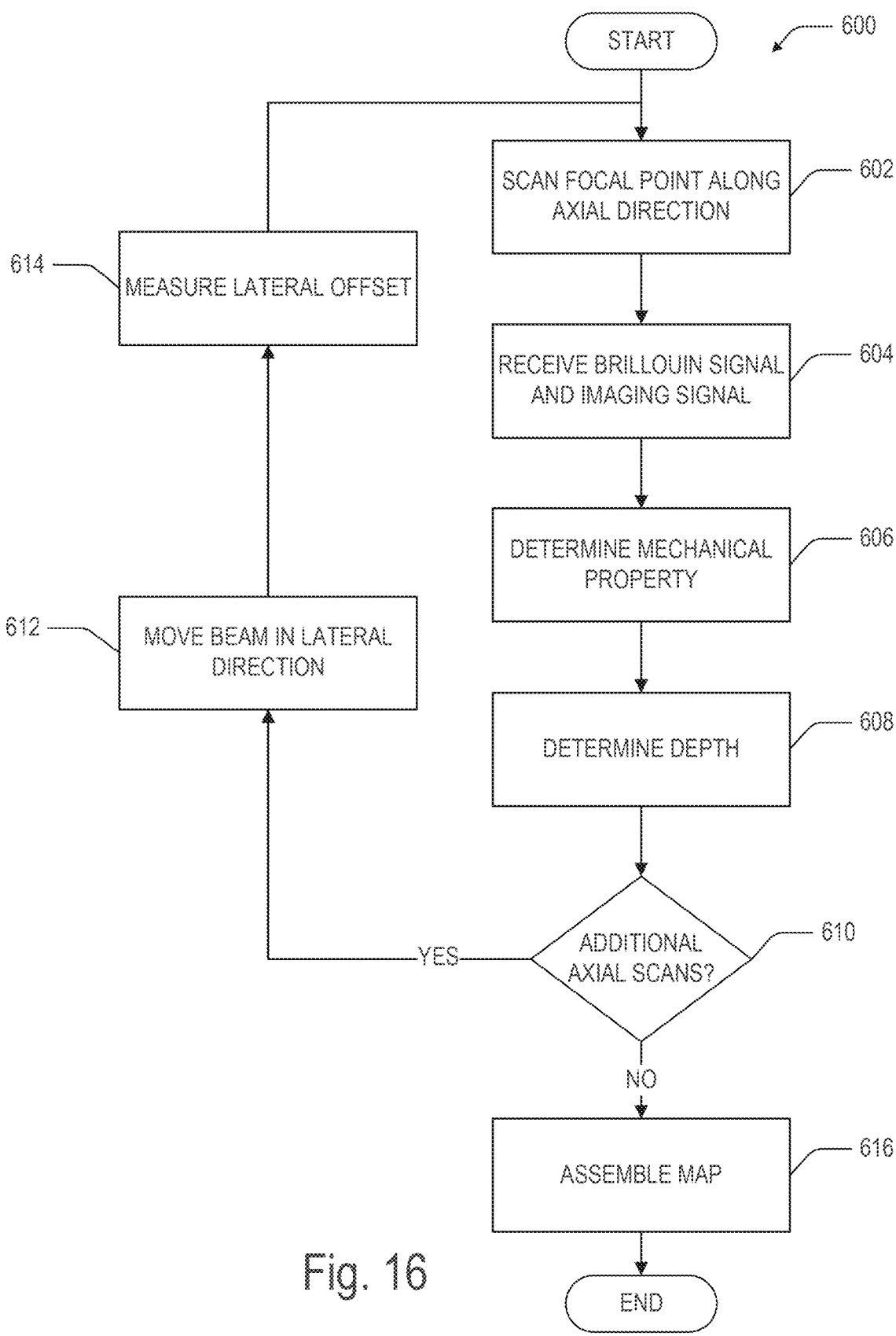
FIG. 16 is a flowchart showing a method of mapping a mechanical property of a medium, in accordance with an aspect of the present disclosure.

Referring to FIG. 16, this disclosure further provides a method 600 of mapping a mechanical property of a medium. At process block 602, the method 600 can include scanning a focal point of a co-registered and/or multiplexed optical beam along an axial direction through the medium. As described above, the co-registered and/or multiplexed optical beam can include a Brillouin probe beam and an imaging sample beam, such as an OCT sample beam or a Scheimpflug sample beam. At process block 604, the method 600 can include receiving a Brillouin signal generated by the Brillouin probe beam and a three-dimensional imaging signal generated by the imaging sample beam. The three-dimensional imaging signal can be an OCT signal generated by the OCT sample beam or a Scheimpflug signal generated by the Scheimpflug sample beam. At process block 606, the method 600 can include determining, using a processor and the Brillouin signal, the mechanical property of the medium for at least one point along the axial direction. At process block 608, the method 600 can include determining, using the processor and the three-dimensional imaging signal, a depth of the at least one point along the axial direction. At decision block 610, the method 600 can include determining if additional axial scans in a lateral direction are desired. If the answer to decision block 610 is YES, then the method 600 proceeds to process block 612. If the answer to decision block 610 is NO, then the method 600 proceeds to process block 616. At process block 612, the method 600 can include shifting the multiplexed optical beam in a lateral direction by a lateral offset. At process block 614, the method 600 can include determining, using the processor and the three-dimensional imaging signal, the lateral offset. After process block 612, and before, during, or after process block 614, the method 600 can repeat process blocks 602, 604, 606, and 608 at the new lateral offset location. The loop of process blocks 612, 614, 602, 604, 606, and 608 can be repeated as many times as necessary to provide a desired three-dimensional map. At process block 616, the method 600 can include assembling the mechanical property map. Notably, a map is but one non-limiting example of a report that may be generated.

In certain aspects, the at least one point of the method 600 can be at least two, at least three, at least four, at least five, or any number of points as time, resolution, and the size of the medium being investigated allow. The at least one point can be a plurality of points.

Figure 17:
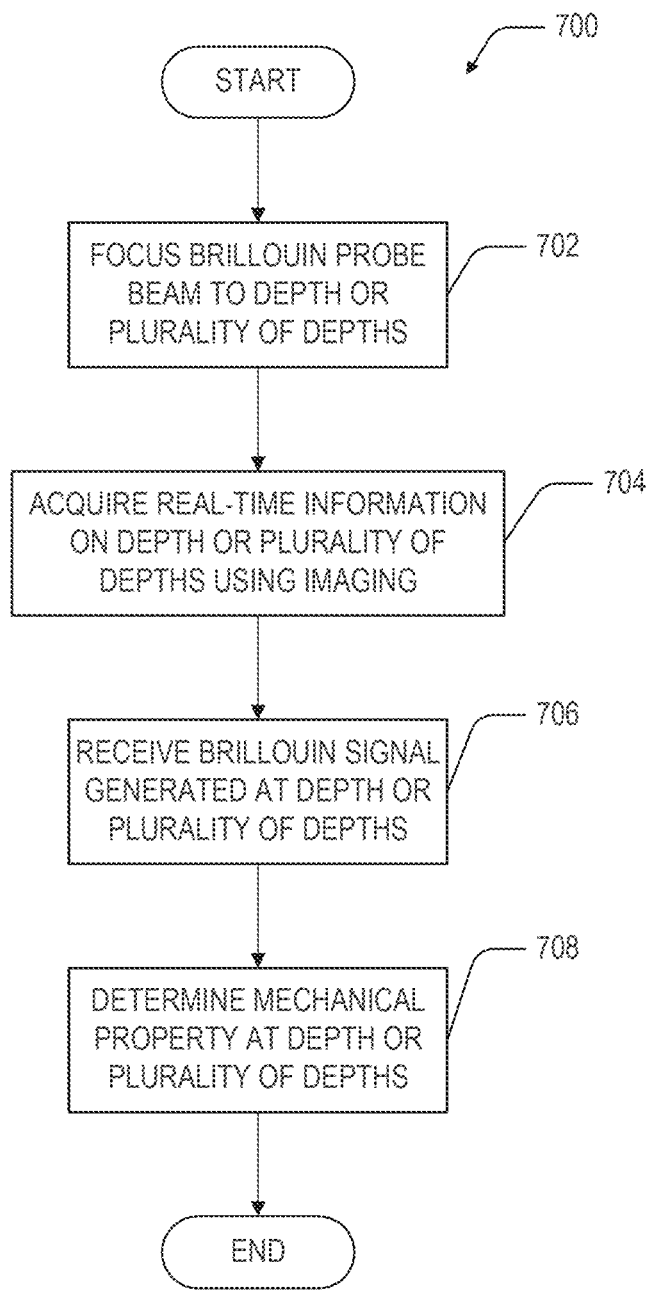
FIG. 17 is a flowchart showing a method of mapping a mechanical property of a medium, in accordance with an aspect of the present disclosure.

Referring to FIG. 17, this disclosure provides a method 700 of measuring or mapping a mechanical property of a medium. At process block 702, the method 700 can include focusing a Brillouin probe beam of a Brillouin spectrometer to a focus at a depth or a plurality of different depths of the medium. At process block 704, the method 700 can include acquiring real-time information on the depth of plurality of different depths using a three-dimensional imaging system, such as OCT or a Scheimpflug camera system. At process block 706, the method 700 can include receiving a Brillouin signal generated by the Brillouin probe beam at the depth or at each of the plurality of different depths. At process block 708, the method 700 can include determining, using a process and the Brillouin signal, the mechanical property of the medium at the depth or at each of the plurality of different depths. The method 700 can be repeated at different lateral positions of the medium.

In certain aspects, the medium being interrogated can be a tissue. In certain aspects, the tissue can be a cornea, a lens, or other tissue types known to a person having ordinary skill in the art to be suitable for interrogation by the systems and methods described herein.

In certain aspects, the mechanical property can be elasticity or other mechanical properties known to a person having ordinary skill in the art to be measurable by the systems and methods described herein.

In vivo Brillouin imaging of keratoconus corneas revealed that the difference in the Brillouin shift in the advanced cone is 50-100 MHz or a 1-2% change. This corresponds to approximately 70-140% decrease in shear modulus (G', 1 Hz). To detect earlier stages of keratoconus, it would thus be necessary to detect differences less than 10 MHz. Using the Brillouin references 525 described above, the spectral axis of the Brillouin spectrometer can be calibrated to achieve absolute frequency accuracy of better than 10 MHz.

In one aspect, in general, a method for obtaining information associated with an anatomical sample includes: providing at least one first electro-magnetic radiation to the anatomical sample so as to generate at least one acoustic wave in the anatomical sample, wherein at least one second electro-magnetic radiation is produced based on the at least one acoustic wave; receiving at least one portion of the at least one second electro-magnetic radiation; providing at least one third electro-magnetic radiation to the sample so as to generate at least one fourth electro-magnetic radiation that comprises a backscattered portion of the third electro-magnetic radiation that has been backscattered from the anatomical sample; receiving at least one portion of the fourth electro-magnetic radiation in an interferometer that includes (1) a sample arm optical path including the anatomical sample, and (2) a reference arm optical path, wherein the reference arm optical path provides a fixed optical delay during operation; and determining at least one biomechanical property of a first portion of the anatomical sample based on the at least one portion of the at least one second electro-magnetic radiation and determining depth profile information associated with the first portion of the anatomical sample based on at least one interference signal from the interferometer.

Aspects can include one or more of the following features. The at least one second electro-magnetic radiation is produced based on Brillouin scattering. The method further includes forming a biomechanical image of the anatomical sample based on the determined biomechanical properties of a plurality of portions of the anatomical sample. The interferometer is included in an imaging system that provides a tomographic image of the anatomical sample that is associated with the biomechanical image of the anatomical sample. The imaging system comprises an optical frequency domain imaging (OFDI) system that uses a frequency swept source to provide the interference signal as a function of frequency. The imaging system comprises a spectral domain optical coherence tomography (SD-OCT) imaging system uses a spectral separating unit to separate spectral components of the interference signal as a function of the spectral components. The anatomical sample comprises a portion of an eye, and a total power of the first electro-magnetic radiation is limited based on a tolerance before thermal damage can occur.

In another aspect, in general, an arrangement for obtaining information associated with an anatomical sample includes: at least one first arrangement configured to provide at least one first electro-magnetic radiation to the anatomical sample so as to generate at least one acoustic wave in the anatomical sample, wherein at least one second electro-magnetic radiation is produced based on the at least one acoustic wave; at least one second arrangement configured to receive at least one portion of the at least one second electro-magnetic radiation; at least one third arrangement configured to providing at least one third electro-magnetic radiation to the sample so as to generate at least one fourth electro-magnetic radiation that comprises a backscattered portion of the third electro-magnetic radiation that has been backscattered from the anatomical sample; at least one fourth arrangement that includes an interferometer configured to receive at least one portion of the fourth electro-magnetic radiation, wherein the interferometer includes (1) a sample arm optical path including the anatomical sample, and (2) a reference arm optical path, wherein the reference arm optical path provides a fixed optical delay during operation; and at least one fifth arrangement configured to determine at least one biomechanical property of a first portion of the anatomical sample based on the at least one portion of the at least one second electro-magnetic radiation and to determine depth profile information associated with the first portion of the anatomical sample based on at least one interference signal from the interferometer.

Aspects can have one or more of the following advantages. By combining biomechanical imaging based on Brillouin scattering with a tomographic imaging technique that uses a fixed optical delay in a reference arm optical path, not only can a biomechanical image be co-registered with a depth-resolved tomographic image, but acquisition times are fast enough to enable combined imaging. For example, tomographic imaging techniques such as optical frequency domain imaging (OFDI) or spectral domain optical coherence tomography (SD-OCT) enable imaging without requiring scanning of an optical delay of a reference arm as in some forms of optical coherence tomography.

While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, certain embodiments of the disclosures described herein can be embodied within a form that does not provide all of the features and benefits set forth herein, as some features can be used or practiced separately from others. The scope of certain disclosures disclosed herein is indicated by the appended claims rather than by the foregoing description. All changes which come within the meaning and range of equivalency of the claims are to be embraced within their scope.

We claim:

1. A method of mapping a mechanical property of a medium, the method comprising:
    a) scanning a focal point of a multiplexed optical beam along an axial direction through the medium, the multiplexed optical beam comprising a Brillouin probe beam and an optical coherence tomography (OCT) sample beam;
    b) receiving a Brillouin signal generated by the Brillouin probe beam and an OCT signal generated by the OCT sample beam;
    c) determining, using a processor and the Brillouin signal, the mechanical property of the medium for at least one point along the axial direction;
    d) determining, using the processor and the OCT signal, a depth of the at least one point along the axial direction.

2. The method of claim 1, the method further comprising:
    e) shifting the multiplexed optical beam in a lateral direction by a lateral offset and repeating steps a) through d); and
    f) determining, using the processor and the OCT signal, the lateral offset.

3. The method of claim 2, the method further comprising:
    g) repeating steps e) and f) a plurality of times to produce a three-dimensional map of the mechanical property throughout the medium.

4. The method of any of the preceding claims, the method further comprising isolating the Brillouin signal from the OCT signal.

5. The method of any of the preceding claims, wherein the at least one point is a plurality of points.

6. The method of any of the preceding claims, further comprising generating a report from indicating at least the mechanical property of the medium and the depth of the at least one point.

7. The method of any of the preceding claims, wherein the medium is tissue.

8. The method of claim 7, wherein the tissue is a cornea.

9. A method of measuring a mechanical property of a medium, the method comprising:
    a) focusing a Brillouin probe beam of a Brillouin spectrometer to a focus at a depth in the medium;
    b) acquiring real-time information on the depth using an optical coherence tomography (OCT) sample beam, wherein the Brillouin probe beam and the OCT sample beam are multiplexed;
    c) receiving a Brillouin signal generated by the Brillouin probe beam; and
    d) determining, using a processor and the Brillouin signal, the mechanical property of the medium at the depth.

10. The method of claim 9, the method further comprising moving the focus to a different depth and repeating steps b), c), and d).

11. The method of claim 10, the method further comprising assembling, using the processor, a mechanical property map of the medium.

12. A method of mapping a mechanical property of a medium, the method comprising:
    a) focusing a Brillouin probe beam of a Brillouin spectrometer to a focus at a plurality of different depths in the medium;
    b) acquiring real-time information on the plurality of different depths using an optical coherence tomography (OCT) sample beam, wherein the Brillouin probe beam and the OCT sample beam are multiplexed;
    c) receiving a Brillouin signal generated by the Brillouin probe beam at each of the plurality of different depths; and
    d) determining, using the processor and the Brillouin signal, the mechanical property of the medium at each of the plurality of different depths.

13. The method of claim 11, the method further comprising moving the Brillouin probe beam to a different lateral position of the medium and repeating steps a) to d).

14. The method of claim 12 or 13, the method further comprising assembling, using the processor, a mechanical property map of the medium.

15. An optical system comprising:
    a Brillouin microscope having a Brillouin probe beam; and
    an optical coherence tomography (OCT) system having an OCT sample beam, wherein the Brillouin probe beam and the OCT sample beam are a multiplexed beam, and wherein the optical system comprises multiplex optics configured to deliver the multiplexed beam to a focal point of a sample, to receive a Brillouin signal and deliver the Brillouin signal to the Brillouin microscope, and to receive an OCT signal from the depth of the focal point and deliver the OCT signal to the OCT system.

16. The optical system of claim 15, wherein the Brillouin microscope comprises a Brillouin light source, a Brillouin spectrometer, and Brillouin optics configured to deliver the Brillouin probe beam to the multiplex optics, to receive the Brillouin signal from the multiplex optics, and to deliver the Brillouin signal to the Brillouin spectrometer, wherein the OCT system has an OCT light source, an OCT spectrometer, and OCT optics configured to deliver the OCT sample beam to the multiplex optics and to receive the OCT signal from the multiplex optics.

17. The optical system of claim 15, wherein the multiplexed beam travels through an objective lens that is translatable along an axial direction.

18. The optical system of claim 17, wherein the multiplexed beam travels through a beam scanner that steers the multiplexed beam transverse to the axial direction.

19. The optical system of claim 18, the optical system further comprising one or more motors configured to translate the objective lens or to operate the beam scanner.

20. The optical system of claim 19, the optical system further comprising a processor configured to interpret OCT data from the OCT system and to control the one or more motors based on the OCT data.

21. A method of mapping a mechanical property of a medium, the method comprising:
   a) scanning a focal point of a multiplexed optical beam along an axial direction through the medium, the multiplexed optical beam comprising a Brillouin probe beam and an imaging sample beam;
   b) receiving a Brillouin signal generated by the Brillouin probe beam and an imaging signal generated by the imaging sample beam;
   c) determining, using a processor and the Brillouin signal, the mechanical property of the medium for at least one point along the axial direction; and
   d) determining, using the processor and the imaging signal, a depth of the at least one point along the axial direction.

22. A method of measuring a mechanical property of a medium, the method comprising:
   a) focusing a Brillouin probe beam of a Brillouin spectrometer to a focus at a depth in the medium;
   b) acquiring real-time information on the depth using a three-dimensional imaging system, wherein a focal plane of the three-dimensional imaging system is configured to coincide with the focus of the Brillouin probe beam to determine the information on the depth;
   c) receiving a Brillouin signal generated by the Brillouin probe beam; and
   d) determining, using a processor and the Brillouin signal, the mechanical property of the medium at the depth.

23. A method of measuring a mechanical property of a medium, the method comprising:
   a) focusing a Brillouin probe beam of a Brillouin spectrometer to a focus at a plurality of different depths in the medium;
   b) acquiring real-time information on the plurality of different depths using a three-dimensional imaging system, wherein a focal plane of the three-dimensional imaging system is configured to coincide with the focus of the Brillouin probe beam to determine the information at each of the plurality of different depths;
   c) receiving a Brillouin signal generated by the Brillouin probe beam; and
   d) determining, using a processor and the Brillouin signal, the mechanical property of the medium at the plurality of different depths.

24. An optical system comprising:
   a Brillouin microscope having a Brillouin probe beam; and
   a three-dimensional imaging system having an imaging sample beam, wherein the Brillouin probe beam and the imaging sample beam are a multiplex and/or co-registered beam, and wherein the optical system comprises multiplex optics configured to deliver the multiplexed beam to a focal point of a sample, to receive a Brillouin signal generated by the Brillouin probe beam and deliver the Brillouin signal to the Brillouin microscope, and to receive an imaging signal generated by the imaging sample beam from the depth of the focal point and deliver the imaging signal to the three-dimensional imaging system.

* * * * *